United States Patent [19]

Chibata et al.

[11] 4,455,372

[45] Jun. 19, 1984

[54] METHOD FOR FERMENTATIVE PRODUCTION OF L-PROLINE

[75] Inventors: Ichiro Chibata, Suita; Masahiko Kisumi, Kobe; Masaki Sugiura, Kawanishi; Tsutomu Takagi, Toyonaka, all of Japan

[73] Assignee: Tanabe Seiyaku Co., Ltd., Osaka, Japan

[21] Appl. No.: 422,730

[22] Filed: Sep. 24, 1982

[30] Foreign Application Priority Data

Oct. 6, 1981 [JP] Japan .............................. 56-159829
Jun. 22, 1982 [JP] Japan .............................. 57-107941

[51] Int. Cl.$^3$ ...................... C12P 13/24; C12N 1/20; C12R 1/43
[52] U.S. Cl. ................................. 435/107; 435/253; 435/881
[58] Field of Search ............................... 435/107, 253

[56] References Cited

U.S. PATENT DOCUMENTS 4,224,409  9/1980  Nakamori et al. .................. 435/107

OTHER PUBLICATIONS

Applied and Environmental Microbiology, May 1976, vol. 31, No. 5, pp. 738–742.

Primary Examiner—Lionel M. Shapiro
Attorney, Agent, or Firm—Jordan B. Bierman; Linda Bierman

[57] ABSTRACT

A method for the fermentative production of L-proline which comprises cultivating a L-proline-producing mutant of a microorganism belonging to the genus Serratia in a broth to produce and accumulate L-proline therein and collecting accumulated L-proline. The mutant is preferably that of *Serratia marcescens* which is deficient in L-proline oxidase and is resistant to proline analong under a high osmotic pressure.

15 Claims, No Drawings

METHOD FOR FERMENTATIVE PRODUCTION OF L-PROLINE

The present invention relates to a method for the fermentative production of L-proline.

L-Proline is an important amino acid and a useful additive for drugs and feed.

Various methods have hitherto been known in the fermentative production of L-proline. For example, L-proline can be obtained by cultivating a L-proline-producing wild-type strain or mutant (e.g. an auxotroph, a proline metabolic antagonist-resistant mutant, etc.) of microorganism belonging to the genus Brevibacterium, Micrococcus, Kurthia, Saccharomyces, Bacillus, Escherichia, Microbacterium, Corynebacterium or Arthrobacter in a broth to produce and accumulate L-proline in the broth and collecting the accumulated product (Japanese Patent Publication Nos. 11751/1968, 1198/1969, 6631/1969, 26911/1969, 38557/1971, 38876/1973 and 33190/1976; Japanese Patent Laid Open Publication Nos. 41386/1979, 148096/1980 and 2691/1982). However, the use of a microorganism belonging to the genus Serratia in the fermentative production of L-proline has not been reported heretofore in the prior art.

As a result of the present inventors' intensive study on the fermentative production of L-proline, it has been found that L-proline can be produced and accumulated in a substantial amount in a broth by using a mutant of a microorganism belonging to the genus Serratia which is deficient in a L-proline-degrading enzyme and resistant to a proline analog, while, usually, a microorganism belonging to the genus Serratia does not produce and accumulate L-proline since it has a high L-proline-degrading enzymatic activity and L-proline biosynthesis thereof is controlled by feedback (control) mechanisms.

Further, it has been also found that a mutant having remarkably improved L-proline productivity can be obtained by increasing sensitivity of a L-proline-producing mutant of a microorganism belonging to the genus Serratia to a metabolic antagonist of L-proline under a specific condition. That is, in order to obtain a mutant which can produce and accumulate a certain amino acid in a remarkable amount, it is generally advantageous to increase its sensitivity to a metabolic antagonist of the amino acid (i.e. to enhance resistance to the antagonist). However, a mutant which accumulates the amino acid even in a small amount is usually more or less resistant to a metabolic antagonist of the amino acid and it is difficult to further increase its sensitivity to the antagonist or to give resistance to another metabolic antagonist of the same amino acid. Only a few methods have been known to further increase sensitivity of a metabolic antagonist resistant mutant, in which carbon sources used in cultivation of the mutant are varied [Method in Enzymology, Vol. 22, pp 86–89 (1971); Journal of Bacteriology, Vol. 109, pp 365–372 (1972); ibid., Vol. 133, pp 1232–1236 (1978); ibid., Vol. 141, pp 205–212 (1980)]. On the contrary, it has been surprisingly found that a L-proline-producing mutant of a microorganism belonging to the genus Serratia remarkably increases its sensitivity to a metabolic antagonist of L-proline when it is treated under a high osmotic pressure and, when this phenomenon is applied in the isolation of a proline analog resistant mutant, a mutant having remarkably improved L-proline productivity can be obtained.

One object of the present invention is to provide a method for the fermentative production of L-proline in which a microorganism belonging to the genus Serratia is used.

Another object of the present invention is to provide a method for the fermentative production of L-proline in which L-proline can be produced in a good yield by using a microorganism belonging to the genus Serratia.

These objects as well as other objects and advantages of the present invention will become apparent to those skilled in the art from the following description.

According to the present invention, there is provided a method for the fermentative production of L-proline which comprises cultivating a L-proline-producing mutant of a microorganism belonging to the genus Serratia, preferably, the mutant which is resistant to proline analog under a high osmotic pressure (i.e., the mutant which is resistant to proline analog in a culture medium containing 0.1 to 0.7 M of a substance for increasing osmotic pressure thereof such as alkali metal halide or sucrose), in a broth to produce and accumulate L-proline in the broth and collecting accumulated L-proline.

The L-proline-producing mutant to be used in the present invention is that of a microorganism belonging to the genus Serratia which is deficient in a L-proline-degrading enzyme such as L-proline oxidase as well as resistant to a proline analog such as 3,4-dehydro-DL-proline (DHP), L-thiazolidine-4-carboxylic acid (TAC) or L-azetidine-2-carboxylic acid (AZC). Particularly, the mutant which is resitant to proline analog under a high osmotic pressure is preferred. Examples of the mutant are those of *Serratia marcescens* which are deficient in L-proline oxidase and resistant to one or more proline analogs. Preferred examples of the mutant are the mutant of *Serratia marcescens* which is deficient in L-proline oxidase and resistant to both DHP and TAC, the mutant of *Serratia marcescens* which is deficient in L-proline oxidase and is resistant to TAC under a high osmotic pressure and the mutant of *Serratia marcescens* which is deficient in L-proline oxidase and is resistant to AZC under a high osmotic pressure.

Representative mutants to be used in the present invention have been deposited with Fermentation Research Institute, Agency of Industrial Science and Technology, 1-3, Higashi 1 Chome Yatabe-Machi Tsukuba-gun Ibaraki-ken 305, Japan (hereinafter, referred to as FERM). They are *Serratia marcescens* strain DTr-12 (FERM-BP No. 171), *Serratia marcescens* strain OTr-88 (FERM-BP No. 172) and *Serratia marcescens* strain OAr-80 (FERM-BP No. 173).

The mutant to be used in the present invention can be obtained by subjecting a microorganism belonging to the genus Serratia to a mutagenizing treatment to induce L-proline-degrading enzyme deficiency and then further subjecting the resulting mutant to a mutagenizing treatment to induce the desired proline analog resistance.

For example, the mutant which is deficient in a L-proline-degrading enzyme and resistant to both DHP and TAC can be obtained as follows:

A starting microorganism such as *Serratia marcescens* strain Sr41 (this strain has bacteriological characteristics of *Serratia marcescens* as described in Bergey's Manual of Determinative Bacteriology 8th Edition, page 326) is subjected to a mutagenizing treatment such as irradiation with ultraviolet or treatment with a mutagen (e.g. N-methyl-N'-nitro-N-nitrosoguanidine, ethyl methanesulfonate, etc.) to induce mutation. Then, the microorganism thus treated is cultivated at 30° C. for 3 to 5 days on agar plates (e.g. those of Davis's minimal medium) containing as a main carbon or nitrogen source L-proline and the resulting small colonies are picked up to isolate a L-proline-degrading enzyme deficinet mutant. The resulting L-proline-degrading enzyme deficient mutant is further subjected to a mutagenizing treatment to induce mutation and cultivated at 30° C. for 1 to 3 days on agar plates (e.g. those of Davis's minimal medium) containing DHP (e.g. in the amount of 0.2 mg/ml). The colonies thus formed are picked up to isolate a mutant which is deficient in a L-proline-degrading enzyme and resistant to DHP. Further, this DHP resistant mutant is subjected to a mutagenizing treatment and cultivated at 30° C. for 3 to 5 days on agar plates (e.g. those of Davis's minimal medium containing 0.5% of disodium succinate instead of glucose) containing TAC (e.g. in the amount of 1.0 mg/ml). The colonies thus formed are picked up to isolate the desired mutant which is deficient in a L-proline-degrading enzyme and resistant to both DHP and TAC. A representative of the mutant thus obtained is Serratia marcescens strain DTr-12 (FERM-BP No. 171) which is deficient in L-proline oxidase and resistant to both DHP and TAC.

The mutant which is deficient in a L-proline-degrading enzyme and is resistant to proline analog under a high osmotic pressure can be obtained from the above-obtained L-proline-degrading enzyme deficient mutant by subjecting the mutant to a mutagenizing treatment as described above, cultivating the mutant at 30° C. for 3 to 5 days on agar plates (e.g. those of Davis's minimal medium) containing a proline analog and a substance for increasing osmotic pressure such as alkali metal halide (e.g., sodium chloride, potassium chloride, lithium chloride) or sucrose and picking up the resulting colonies to isolate the desired mutant. Alternatively, this type of mutant can be obtained by subjecting a mutant of Serratia marcescens which is deficient in a L-proline-degrading enzyme and resistant to a proline analog to a mutagenizing treatment, cultivating the mutant at 30° C. for 3 to 5 days on agar plates containing a proline analog and the substance for increasing osmotic pressure and picking up the resulting colonies to isolate the desired mutant. Usually, it is preferable that 0.1 to 0.7 M, especially 0.2 to 0.5 M of the substance for increasing osmotic pressure is present in a culture medium. Representatives of the mutant thus obtained are Serratia marcescens strain OTr-88 (FERM-BP No. 172) which is deficient in L-proline oxidase and is resistant to TAC in the presence of 0.2 M of sodium chloride and Serratia marcescens strain OAr-80 (FERM-BP No. 173) which is deficient in L-proline oxidase and is resistant to AZC in the presence of 0.2 M of sodium chloride.

The preparation of the mutant to be used in the present is not limited to those described above and the L-proline-producing mutant can be also obtained, for example, by changing the order of the above treatments for inducing L-proline-degrading enzyme deficiency and proline analog resistance or by separately preparing plural mutants each of which having a separate characteristic such as L-proline-degrading enzyme deficiency or proline analog resistance and treating these mutants according to a genetic recombination technique such as transduction.

The following test illustrates increase of sensitivity of the mutant to a proline analog under a high osmotic pressure.

Serratia marcescens strain DTr-12 was cultivated in a broth at 30° C. for 24 hours. One loopful of the resulting microbial cells was suspended in physiological saline and the suspension was inoculated in a broth (pH 7.0, 3 ml) composed of glucose (0.5 w/v %), ammonium sulfate (0.1 w/v %), dipotassium hydrogen phosphate (0.7 w/v %), potassium dihydrogen phosphate (0.3 w/v %) and magnesium sulfate (0.01%) and containing a predetermined amount of sodium chloride and/or a proline analog. The concentration of the microbial cells in the broth was about $5 \times 10^7$ cells/ml. The broth was incubated with shaking at 30° C. for 8 to 24 hours. After incubation, growth of the microorganism was determined by measuring the turbidity of the broth thus cultivated at 660 nm. Relative growth (%) of each culture was calculated on the basis of the growth of the microorganism in the broth containing no proline analong as 100 when the turbidity thereof reached to 1.0. The results are shown in Table 1.

TABLE 1

| Strain | NaCl concentration (M) | Relative growth (%) Proline analogs | | | |
|---|---|---|---|---|---|
| | | Absent | DHP $10^{-3}$ M | TAC $10^{-2}$ M | AZC $10^{-3}$ M |
| Serratia marcescens strain DTr-12 | 0 | 100 | 110 | 95 | 95 |
| | $4 \times 10^{-1}$ | 100 | 4 | 5 | 5 |

As is obvious from Table 1, in comparison with cultivation using the broth containing no sodium chloride, DTr-12 strain increases its sensitivity to the proline analog in the presence of sodium chloride. Besides, this inhibition is partially or wholly removed by addition of L-proline to the broth.

The method of the present invention can be carried out by cultivating the L-proline-producing mutant in a broth to produce and accumulate L-proline in the broth and collecting L-proline thus accumulated.

The broth to be used for the production of L-proline in the present invention suitably contains 10 to 20 w/v % of a carbon source such as saccharides (e.g. glucose, sucrose, molasses, etc.), organic acids (e.g. succinic acid, citric acid, fumaric acid, etc.), sugar alcohols (e.g. glycerol) or the like; 1 to 5 w/v % of a nitrogen source such as organic ammonium salts (e.g. ammonium succinate, ammonium fumarate, etc.), inorganic ammonium salts (e.g. ammonium sulfate, ammonium chloride, etc.), urea or the like; and 0 to 1 w/v % of an organic nutrient such as corn steep liquor, peptone, yeast extract, meat extract or the like. Further, a small amount of potassium phosphate, magnesium sulfate, ferrous sulfate or the like may be added to the broth. Calcium carbonate or, if necessary, aqueous ammonia or citric acid may be also added to the broth so as to maintain the pH thereof at 6 to 8. Furthermore, optionally, a precursor for L-proline biosynthesis such as L-glutamic acid, L-aspartic acid or the like may be also added to the broth.

According to the method of the present invention, a large amount of L-proline can be produced and accumulated in the broth by inoculating the above-proline-producing mutant into the broth and incubating at 25° to 40° C. for 2 to 6 days under an aerobic condition such as shaking or aeration.

After cultivation, L-proline thus accumulated can be readily separated and recovered from the broth by conventional separation and purification techniques, for example, by removing microbial cells and other insoluble substances from the broth, adsorbing L-proline to an ion exchange resin, eluting adsorbed L-proline with aqueous ammonia, concentrating the eluent and crystallizing L-proline.

The following preparations and examples further illustrate the present invention but are not to be construed to limit the scope thereof. In the examples, the production of L-proline was confirmed by paper chromatography using ninhydrin reaction and isatin reaction and the quantitative analysis thereof was carried out by a bioassay using *Leuconostoc mesenteroides* P-60.

Preparation 1

Preparation of *Serratia marcescens* strain DTr-12

A small amount of *Serratia marcescens* strain Sr41 was inoculated in a broth and cultivated at 30° C. When the concentration of microbial cells in the broth was reached to about $10^9$ cells/ml, an aqueous solution of N-methyl-N'-nitro-N-nitrosoguanidine (1 mg/ml) was added to the broth in such an amount that the concentration of N-methyl-N'-nitro-N-nitrosoguanidine became 0.25 mg/ml and the broth was incubated at 30° C. for 20 minutes. After separation of microbial cells by centrifugation, cells were washed with physiological saline and a fresh broth was added. After incubation at 30° C. for 6 hours, microbial cells were again separated from the broth by centrifugation and suspended in physiological saline. The suspension was diluted with physiological saline to adjust the concentration of cells to about $10^3$ cells/ml. The suspension (0.1 ml) was spread on agar plates containing L-proline as main nitrogen source (glucose (0.5 w/v %), L-proline (0.2 w/v %), ammonium sulfate (0.0002 w/v %), dipotassium hydrogen phosphate (0.7 w/v %), potassium dihydrogen phosphate (0.3 w/v %), magnesium sulfate heptahydrate (0.01 w/v %) and agar (1.5 w/v %)) and incubated at 30° C. for 3 days. The resulting small colonies were picked up and L-proline oxidase activities thereof were determined according to the method described by Dendinger et al., Journal of Bacteriology, Vol. 103, pp 144–152 (1970) to obtain a L-proline oxidase deficient mutant.

The L-proline oxidase deficient mutant thus obtained was treated with N-methyl-N'-nitro-N-nitrosoguanidine and worked up as described above to obtain a cell suspension containing about $10^9$ cells/ml. The suspension (0.1 ml) was spread on agar plates (glucose (0.5 w/v %), ammonium sulfate (0.1 w/v %), dipotassium hydrogen phosphate (0.7 w/v %), potassium dihydrogen phosphate (0.3 w/v %), magnesium sulfate heptahydrate (0.01 w/v %) and agar (1.5 w/v %)) containing DHP (0.2 mg/ml) and cultivated at 30° C. for 2 days. The resulting colonies were picked up and L-proline productivities thereof were determined by cultivating them in the broth described in Example 1 hereinafter to obtain a L-proline oxidase deficient and DHP resistant mutant.

The L-proline oxidase deficient and DHP resistant mutant thus obtained was treated with N-methyl-N'-nitro-N-nitrosoguanidine and worked up as described above to obtain a cell suspension. The suspension (0.1 ml) was spread on agar plates (disodium succinate (0.5 w/v %), ammonium sulfate (0.1 w/v %), dipotassium hydrogen phosphate (0.3 w/v %), potassium dihydrogen phosphate (0.3 w/v %), magnesium sulfate heptahydrate (0.01 w/v %) and agar (1.5 w/v %)) containing TAC (1.0 mg/ml) and cultivated at 30° C. for 4 days. The resulting colonies were picked up and L-proline productivities thereof were determined by cultivating them in the broth described in Example 1 hereinafter to obtain the desired *Serratia marcescens* strain DTr-12.

Preparation 2

Preparation of *Serratia marcescens* strain OTr-88

The L-proline oxidase deficient and DHP resistant mutant obtained in Preparation 1 was treated with N-methyl-N'-nitro-N-nitrosoguanidine and worked up as described in Preparation 1 to obtain a cell suspension containing about $10^9$ cells/ml. The suspension (0.1 ml) was spread on agar plates (disodium succinate (0.5 w/v %), ammonium sulfate (0.1 w/v %), dipotassium hydrogen phosphate (0.7 w/v %), potassium dihydrogen phosphate (0.3 w/v %), magnesium sulfate heptahydrate (0.01 w/v %) and agar (1.5 w/v %)) containing TAC (1.0 mg/ml) and sodium chloride ($5 \times 10^{-1}$ M) and cultivated at 30° C. for 6 days. The resulting colonies were picked up and L-proline productivities thereof were determined by cultivating them in the broth described in Example 2 hereinafter to obtain the desired *Serratia marcescens* strain OTr-88.

Preparation 3

Preparation of *Serratia marcescens* strain OAr-80

*Serratia marcescens* strain DTr-12 obtained in Preparation 1 was treated with N-methyl-N'-nitro-N-nitrosoguanidine and worked up as described in Preparation 1 to obtain a cell suspension containing about $10^9$ cells/ml. The suspension (0.1 ml) was spread on agar plates (disodium succinate (0.5 w/v %), ammonium sulfate (0.1 w/v %), dipotassium hydrogen phosphate (0.7 w/v %), potassium dihydrogen phosphate (0.3 w/v %), magnesium sulfate heptahydrate (0.01 w/v %) and agar (1.5 w/v %)) containing AZC (0.3 mg/ml) and sodium chloride ($2 \times 10^{-1}$ M) and cultivated at 30° C. for 4 days. The resulting colonies were picked up and L-proline productivities thereof were determined by cultivating them in the broth described in Example 3 hereinafter to obtain the desired *Serratia marcescens* strain OAr-80.

EXAMPLE 1

A broth (pH 7.0, 15 ml) containing sucrose (15 w/v %), urea (2 w/v %), dipotassium hydrogen phosphate (0.1 w/v %), magnesium sulfate heptahydrate (0.05 w/v %), corn steep liquor (0.6 w/v %) and calcium carbonate (1 w/v %) was placed in a 500 ml shaking flask and sterilized by autoclaving (sucrose was separately sterilized and added to the broth aseptically). One loopful of *Serratia marcescens* strain DTr-12 which was previously cultivated on bouillon slant at 30° C. overnight was inoculated into the broth and incubated at 30° C. for 72 hours with shaking (140 r.p.m., 7 cm stroke). After incubation, L-proline was produced and accumulated at a concentration of 25.6 mg/ml in the broth.

The resulting broth (1 liter) was collected, heated and filtered to remove micobial cells and other insoluble substances. The filtrate was passed through a column of Amberlite IR-120B (H+ form) to adsorb L-proline. The column was washed with water and eluted with 5% aqueous ammonia. The eluent was concentrated under a reduced pressure, cooled and allowed to stand to crystallize L-proline (18.0 g).

EXAMPLE 2

A broth (pH 7.0, 15 ml) containing sucrose (15 w/v %), urea (2.5 w/v %), dipotassium hydrogen phosphate (0.1 w/v %), magnesium sulfate heptahydrate (0.05 w/v %), ferrous sulfate heptahydrate (0.0002 w/v %), yeast extract (0.5 w/v %) and calcium carbonate (3 w/v %) was placed in a 500 ml shaking flask and sterilized by autoclaving (sucrose was separately sterillized and added to the broth aseptically). One loopful of *Serratia marcescens* strain OTr-88 which was previously cultivated on bouillon slant overnight was inoculated into the broth and incubated at 30° C. for 72 hours with shaking (140 r.p.m., 7 cm stroke). After incubation, L-proline was produced and accumulated at a concentration of 36.4 mg/ml in the broth.

EXAMPLE 3

A broth (pH 7.0, 15 ml) containing sucrose (20 w/v %), urea (3 w/v %), dipotassium hydrogen phosphate (0.1 w/v %), magnesium sulfate heptahydrate (0.05 w/v %), ferrous sulfate heptahydrate (0.0002 w/v %), corn steep liquor (0.5 w/v %) and calcium carbonate (3 w/v %) was placed in a 500 ml shaking flask and sterilized by autoclaving (sucrose was separately sterillized and added to the broth aseptically). One loopful of *Serratia marcescens* strain OAr-80 which was previously cultivated on bouillon slant overnight was inoculated into the broth and incubated at 30° C. for 96 hours with shaking (140 r.p.m., 7 cm stroke). After incubation, L-proline was produced and accumulated at a concentration of 62.5 mg/ml in the broth.

The resulting broth (1 liter) was collected, heated and filtered to remove microbial cells and other insoluble substances. The filtrate was passed through a column of Amberlite IR-120B (H+ form) to adsorb L-proline. The column was washed with water and eluted with 5% aqueous ammonia. The eluent was concentrated under a reduced pressure, cooled and allowed to stand to crystallize L-proline (40.6 g).

What is claimed is:

1. A method for the fermentative production of L-proline which comprises cultivating a L-proline-producing mutant of *Serratia marcescens* in a broth to produce and accumulate L-proline therein and collecting accumulated L-proline, said mutant being deficient in L-proline oxidase and resistant to proline analogs.

2. The method of claim 1, wherein said mutant is resistant to said proline analog at a high osmotic pressure.

3. The method of claim 1, wherein said mutant is resistant to both 3,4-dehydro-DL-proline and L-thiazolidine-4-carboxylic acid.

4. The method of claim 3, wherein said mutant is *Serratia marcescens* strain DTr-12, FERM-BP No. 171.

5. The method of claim 2, wherein said mutant is resistant to L-thiazolidine-4-carboxylic acid in the presence of 0.5 M of sodium chloride.

6. The method of claim 5, wherein said mutant is *Serratia marcescens* strain OTr-88, FERM-BP No. 172.

7. The method of claim 2, wherein said mutant is resistant to L-azetidine-2-carboxylic acid in the presence of 0.2 M of sodium chloride.

8. The method of claim 7, wherein said mutant is *Serratia marcescens* strain OAr-80. FERM-BP No. 173.

9. The method of claim 1, wherein said cultivation is carried out at 25° to 40° C. for 2 to 6 days under aerobic conditions.

10. The method of claim 1, wherein said broth contains 10 to 20 w/v % of a carbon source, 1 to 5 w/v % of a nitrogen source and 0 to 1 w/v % of an organic nutrient and pH thereof is 6 to 8.

11. The method of claim 1, wherein *Serratia marcescens* strain DTr-12, FERM-BP No. 171, is cultivated at 25° to 40° C. for 2 to 6 days in a broth of pH 6 to 8 containing 10 to 20 w/v % of a carbon source, 1 to 5 w/v % of a nitrogen source and 0 to 1 w/v % of an organic nutrient under an aerobic condition.

12. The method of claim 1, wherein *Serratia marcescens* strain OTr-88, FERM-BP No. 172, is cultivated at 25° to 40° C. for 2 to 6 days in a broth of pH 6 to 8 containing 10 to 20 w/v % of a carbon source, 1 to 5 w/v % of a nitrogen source and 0 to 1 w/v % of an organic nutrient under an aerobic condition.

13. The method of claim 1, wherein *Serratia marcescens* strain OAr-80, FERM-BP No. 173, is cultivated at 25° to 40° C. for 2 to 6 days in a broth of pH 6 to 8 containing 10 to 20 w/v % of a carbon source, 1 to 5 w/v % of a nitrogen source and 0 to 1 w/v % of an organic nutrient under an aerobic condition.

14. A method for the fermentative production of L-proline which comprises cultivating a L-proline-producing mutant of *Serratia marcescens* in a broth to produce and accumulate L-proline therein and collecting accumulated L-proline, said mutant being deficient in L-proline oxidase and resistant to proline analogs wherein said mutant is selected from the group consisting of *Serratia marcescens* strain OAr-80, FERM-BP No. 173, *Serratia marcescens* strain OTr-88, FERM-BP No. 172, and *Serratia marcescens* strain DTr-12, FERM-BP No. 171.

15. A culture consisting essentially of a L-proline-producing mutant of *Serratia marcescens*, said mutant being selected from the group consisting of *Serratia marcescens* strain DTr-12, FERM-BP No. 171, *Serratia marcescens* strain OTr-88, FERM-BP No. 172, and *Serratia marcescens* strain OAr-80, FERM-BP No. 173.

* * * * *